United States Patent [19]

Borden

[11] Patent Number: 4,896,048

[45] Date of Patent: Jan. 23, 1990

[54] SCATTERING-TYPE PARTICLE DETECTION DEVICE FOR USE IN HIGH TEMPERATURE PROCESS CHAMBERS

[75] Inventor: Peter G. Borden, Palo Alto, Calif.

[73] Assignee: High Yield Technology, Mountain View, Calif.

[21] Appl. No.: 199,546

[22] Filed: May 27, 1988

[51] Int. Cl.$^4$ ............... G01N 15/07; G01N 21/00
[52] U.S. Cl. ............... 250/574; 356/339; 250/227
[58] Field of Search ............... 250/227, 574, 575, 576; 356/336, 337, 338, 339, 340, 341, 342, 343, 39

[56] References Cited

U.S. PATENT DOCUMENTS

| | | | |
|---|---|---|---|
| 4,291,983 | 9/1981 | Kraft et al. | 250/574 |
| 4,571,079 | 2/1986 | Knollenberg | 356/339 |
| 4,595,291 | 6/1986 | Tatsuno | 356/336 |
| 4,719,360 | 1/1988 | Kontani et al. | 250/574 |
| 4,739,177 | 4/1988 | Borden | 250/574 |
| 4,778,593 | 10/1988 | Yamashita et al. | 356/39 |
| 4,779,003 | 10/1988 | Tatsuno | 250/575 |

Primary Examiner—David C. Nelms
Assistant Examiner—William L. Oen
Attorney, Agent, or Firm—Skjerven, Morrill, MacPherson, Franklin & Friel

[57] ABSTRACT

A particle detector includes optical fiber for conducting short wavelength radiation received from a radiation source through a chamber in which a semiconductor wafer is being processed. Light that is scattered by contaminant particles in the process chamber is sensed by an optical fiber pickup, and pulse signals are generated by a photosensing means to provide an indication of the number of particles within the process chamber.

36 Claims, 4 Drawing Sheets

.1cm PER DIVISION
FIBER DIAMETER 400 μm
FIBER-BALL DIST 1.5mm
BALL DIAMETER 15mm
BALL INDEX OF REF 1.84
LENS NA .25
IMAGE PLANE AT 10mm
2000 RAYS

SCATTERING-TYPE PARTICLE DETECTION DEVICE FOR USE IN HIGH TEMPERATURE PROCESS CHAMBERS

BACKGROUND OF THE INVENTION

1. Field of the Invention

This invention relates to a particle detector for use in vacuum or low pressure process equipment and in particular to a particle sensor that is operable in high temperature environments.

2. Description of Prior Art

Semiconductor wafer fabrication processes are particularly susceptible to yield loss due to particle contamination. Free particles landing on a wafer surface during processing can produce defects in patterns and deposit layers that result in device failure. A primary source of these free particles is the vacuum processing equipment that is used for process steps such as the deposition of dielectric and conductive layers, the plasma etching of patterns, electron beam writing of fine patterns, ion implantation of dopants into the wafer surface, and the dry stripping of photoresist. For example, in the process of depositing glass layers on silicon wafers, glass will also deposit in the process chamber. The glass builds up on the walls of the chamber, eventually breaking off and landing on the wafer being processed in the chamber. Similar problems occur in metal deposition systems and other similar types of equipment. Such contamination adversely affects the very fine patterns of the integrated circuits that are being produced. To achieve efficient and high yield semiconductor manufacture, it is essential to determine when the process chamber is dirty from contamination.

U.S. Pat. No. 4,739,177 describes an airborne particle detector that is remote to the semiconductor process while monitoring contaminant particles in an air sample. However, it is known that in many deposition processes cooling of the gases that are used in the various process steps will result in particle generating reactions. When using a remote sensor whereby a sample needs to be drawn, the particle generating reaction places limitations on the use of the sensor.

The aforementioned patent describes a particle sensor for use in vacuum equipment that incorporates a light source, preferably a laser diode, in the optical detection system. When implementing semiconductor processes at high temperature, such as 800° C. by way of example, the performance of the laser diode light source rapidly degrades. Also, the materials conventionally used in semiconductor processes, such as silicon dioxide and silicon nitride, tend to deposit and coat and adversely affect the elements of the optical system which causes a reduction in the sensitivity of the detector system. Furthermore, the relatively long wavelength of the laser diode source that is normally used, which is about 780 nanometers, limits the sensitivity of the detector system, since light scattering intensity scales as the ratio of particle diameter to wavelength.

Also an additional problem experienced with using laser diodes in high temperature environments is the occurrence of very intense background radiation having a wavelength close to that of the laser diode. The background radiation is generated because the furnace used in the semiconductor manufacturing process acts as a black body source. The higher the temperature of operation, the shorter the wavelength distribution of the radiation will be.

FIG. 1 illustrates the intensity of background radiation due to black body radiation in the bandwidth of 750 to 850 nanometers as a function of temperature. The sensor described in U.S. Pat. No. 4,739,177 typically requires about 100 nanowatts per square centimeter of scattered radiation to sense an 0.5 micron diameter particle. The background radiation exceeds this level of intensity at slightly above 400° C. At about 800° C., the sensor disclosed in the aforementioned patent would saturate. It is apparent that it is difficult to provide a detector that is sensitive to very small particles in the temperature range between 400° C. and 800° C. and above when using a laser diode source that typically emits at 780 nanometers.

SUMMARY

An object of this invention is to provide a particle detector that is capable of operating in a high temperature environment with high sensitivity.

Another object of this invention is to provide an optical detector system that senses particle contamination in a process chamber wherein a semiconductor wafer is being processed.

In accordance with this invention, a particle detector useful for operating at relatively high temperatures with high sensitivity comprises a short wavelength light source, an optical fiber means for receiving radiation from the light source, the optical fiber means passing through a process chamber; an optical fiber bundle pickup for receiving light that is passed through the optical fiber means; and a photosensing means for detecting scattered light produced by the radiation and received by the optical fiber means. A filter is preferably disposed between the optical fiber pickup and the photosensing means to pass short wavelength radiation and to block long wavelength radiation from reaching the photosensing means.

BRIEF DESCRIPTION OF THE DRAWINGS

The invention will be described with reference to the drawings in which:

FIG. 2b is an enlarged view of a portion of the particle detector shown within the dashed line in FIG. 2a;

Similar numerals refer to similar elements throughout the drawings.

DESCRIPTION OF THE PREFERRED EMBODIMENT

Figure 1:
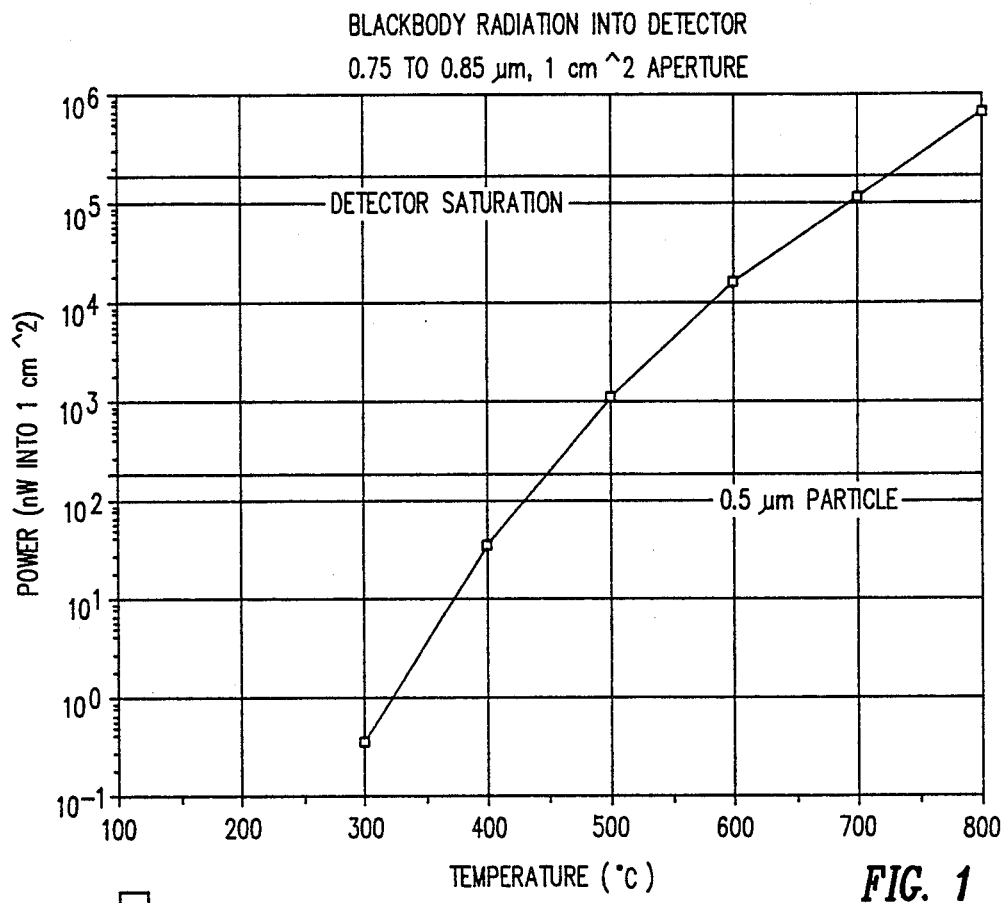
FIG. 1 is a plot of power or radiation intensity of black body background radiation as a function of temperature.
Figure 2A:
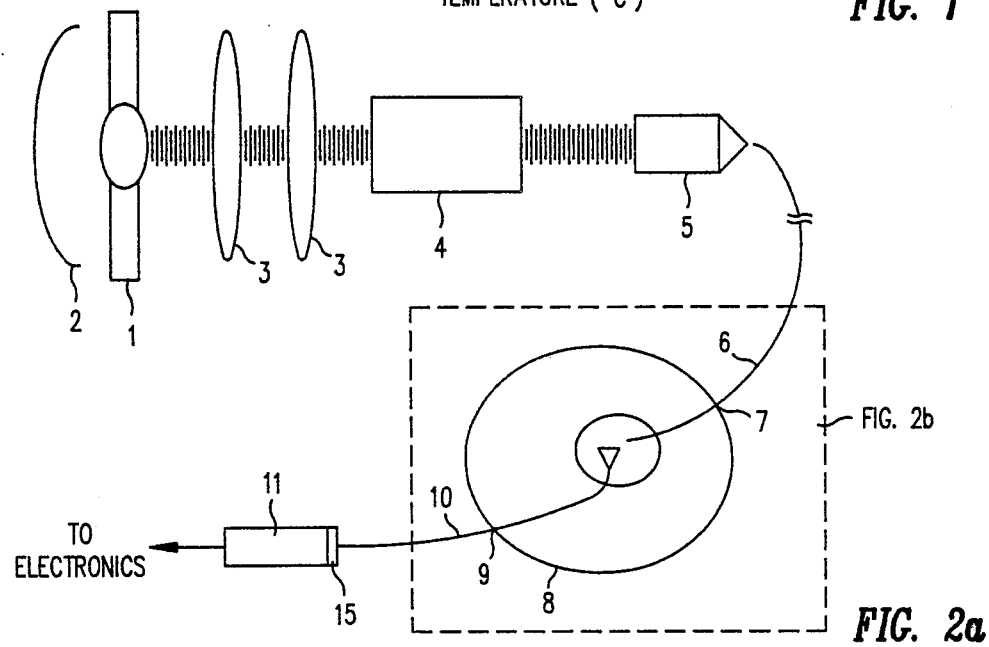
FIG. 2a is a representational view of a particle detector, in accordance with this invention.
Figure 2B:
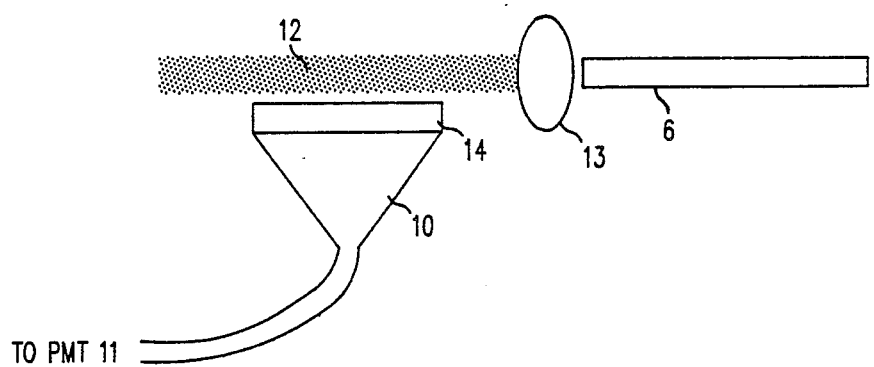

With reference to FIGS. 2a and 2b, a particle sensor useful in high temperature environments comprises a short arc mercury vapor lamp 1. The lamp has an extremely small emission region, 250×250 μm for the case of a 100 watt lamp for example. The lamp affords a concentration of very high power in a small spot, thus making it easier to provide power into an optical fiber. The lamp 1 is disposed in a housing that has a reflector 2 to reflect light that is emitted in the backward direction. The light from the lamp 1 is collimated by lenses 3, and is then passed through a water filter 4 that serves to remove infrared light which would cause excessive heating of an optical fiber tip. The light is then directed into a microscope objective 5 and focused onto an optical fiber 6. The microscope objective 5 has a power of 20× and a numerical aperture of 0.5, by way of example. The fiber preferably has a diameter of 400 microns, a numerical aperture of 0.25 and is made of quartz that is insensitive to high temperatures.

Figure 3:
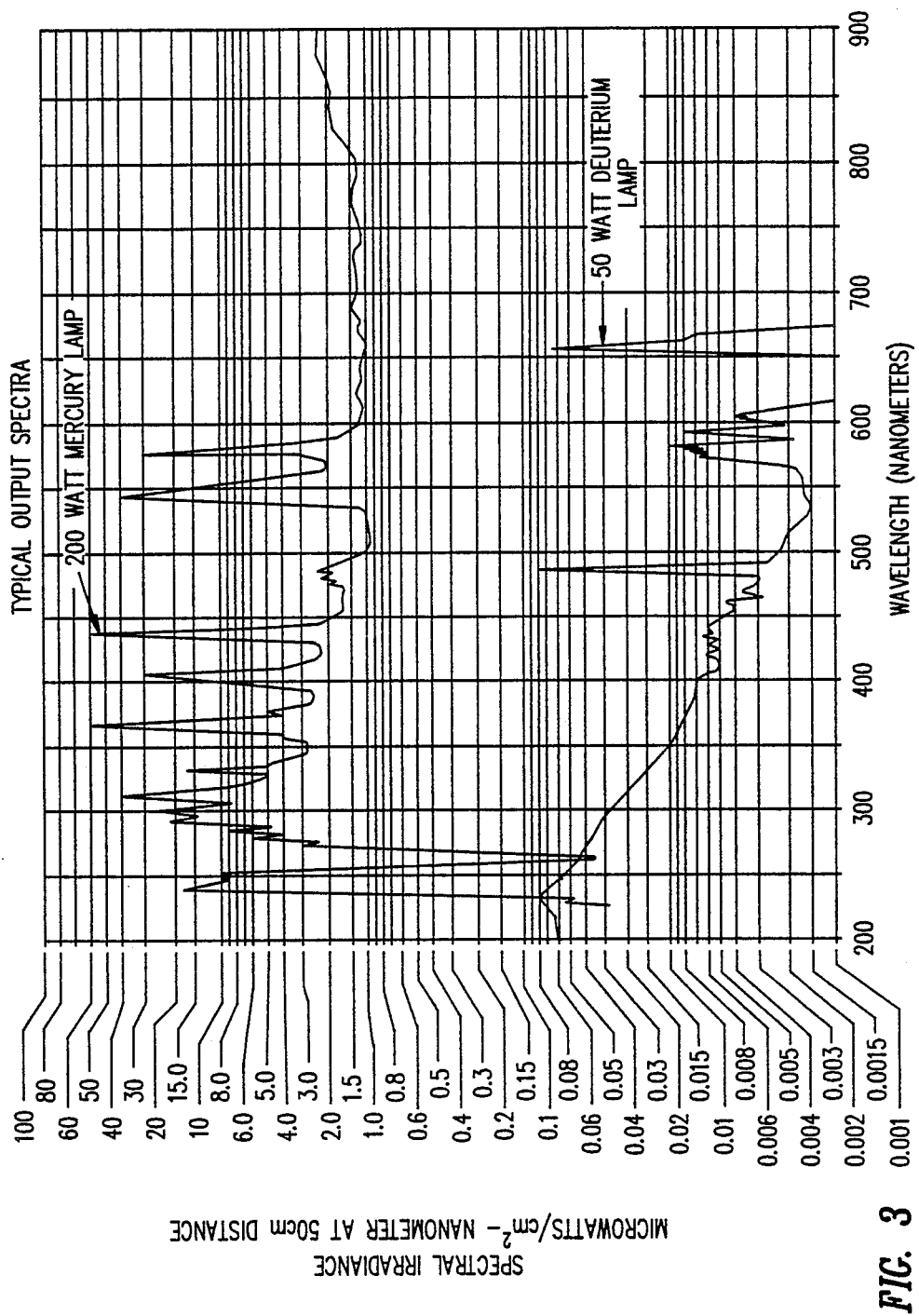
FIG. 3 depicts a mercury vapor spectrum plotting spectral irradiance against wavelength.

The mercury vapor source 1 has a very high specific intensity, providing high power from a small emission region, and has a very short wavelength. The mercury vapor spectrum is illustrated in FIG. 3 and indicates that it is rich in ultraviolet radiation, in the spectrum between 260 and 450 nanometers. In order to pass the short wavelengths, the optical elements used in the particle detector system are made of quartz. However, the short wavelengths below 250 nanometers are filtered out to prevent the short wavelength radiations from inducing chemical reactions in the process chambers.

The optical fiber is passed by means of a standard feedthrough 7 into a process chamber 8 wherein a semiconductor wafer is being processed. The feedthrough 7 is a low loss element that is available commercially or can be made by epoxy sealing the optical fiber 6 through a small hole.

The polished end of fiber 6 emits into a lens 13 to collimate the light beam. In a preferred embodiment, a spherical lens followed by a cylindrical lens are used to form a flat elliptical cross-section beam. The beam 12 has a wide area to detect particles and is of a high intensity.

Particles passing through the beam 12 scatter light to a fiber optic pickup assembly consisting of a ferrule 14 that holds a bundle of fibers 10. The cross-section of the optic pickup assembly is preferably rectangular and mounted close to the light beam 12 that is passed through the lens arrangement 13.

Particles that pass through the beam 12 in the process chamber will scatter light out of the beam. The scattered light will impinge on the pickup and is transmitted out of the process chamber through the fiber bundle 10 and feedthrough 9.

Figure 4:
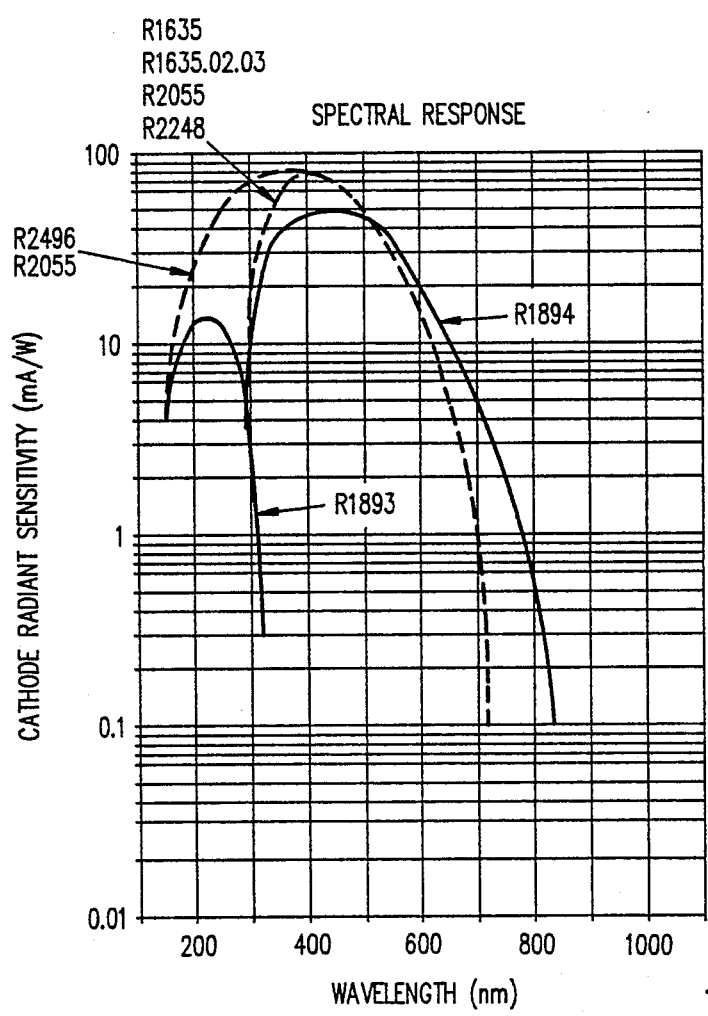
FIG. 4 is a response curve for various photomultipliers showing cathode radiant sensitivity as a function of wavelength.

A photomultiplier (PMT) 11 detects the scattered light that is passed through the fiber bundle 10. In the preferred embodiment a glass filter 15 is used to block the longer wavelength black body radiation in order to prevent saturation of the photomultiplier. Some photomultipliers, such as Hamamatsu Corporation models R2055 and R2496, are ultraviolet sensitive, with a very low response in the infrared. FIG. 4 is a typical spectral response curve for these multipliers, indicating the cathode radiant sensitivity over a range of wavelengths of interest. The photomultiplier tubes may not require a filter 15 unless the temperature in the process chamber is very high, above 700° C. for example.

The scattered light produced by the presence of particles in the process chamber will cause the photomultiplier to produce pulse signals that will be representative of the number of particles that appear in the process chamber and that are sensed. The pulse signals are AC coupled to amplifiers in an electronics system to filter out background DC response from ambient light. The pulses are counted by means of standard digital electronics and will provide an indication of ho many particles have passed through the light beam.

An advantage of the optical detection system of this invention is that although the lens and fiber optic pickups admit thin coatings of transparent materials, such as silicon dioxide and silicon nitride, there is virtually no degradation in optical performance. For example, if the detection system is mounted in a process chamber in which silicon dioxide is being deposited on semiconductor wafers, then silicon dioxide will also deposit on the lens 13 and fiber pickup. The silicon dioxide may also be deposited on the end of optic fiber 6, but the fiber end can be protected if so desired. The coatings resulting from silicon dioxide deposition are very thin, which may be about a micron for each deposition, so that the coatings have very little effect, if any, on the optical system.

Figure 5:
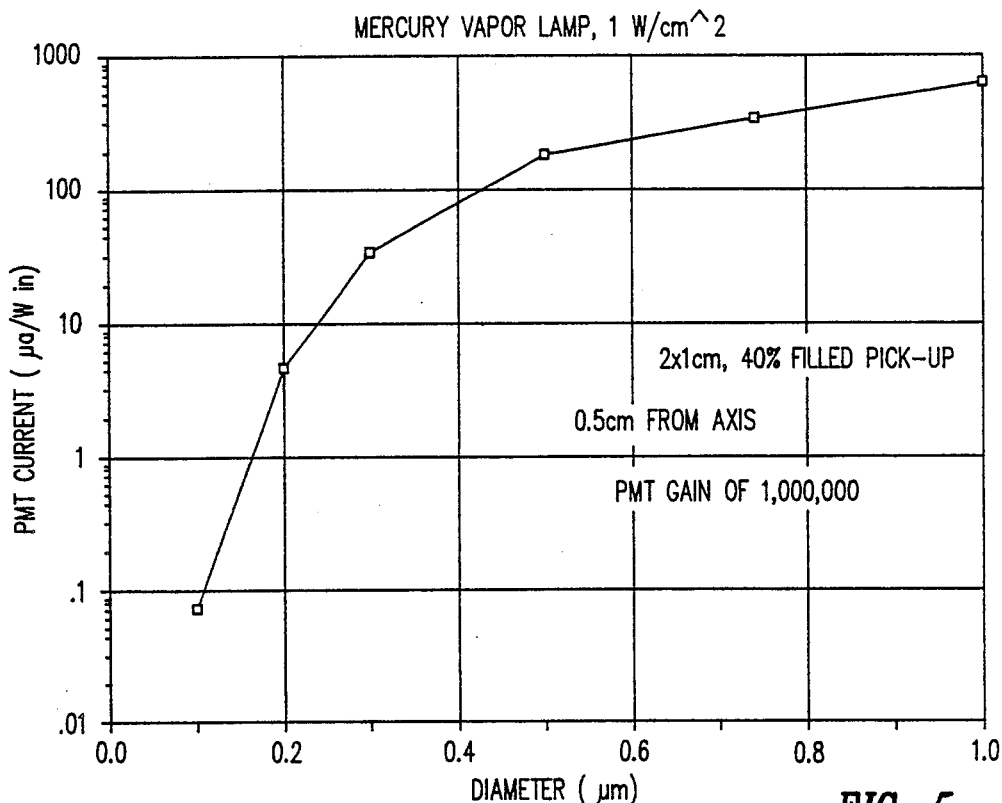
FIG. 5 is a plot of photomultiplier current as a function of particle diameter.

FIG. 5 shows the PMT current as a function of particle diameter, assuming 1 watt per square centimeter of incident power, as measured for the system disclosed herein. The pickup 14 is assumed to have a dimension of $2 \times 1$ cm and is filled 40% with fibers. It is also been found that with this system 44 milliwatts of optical radiation can be launched from the end of the optic fiber.

Figure 6:
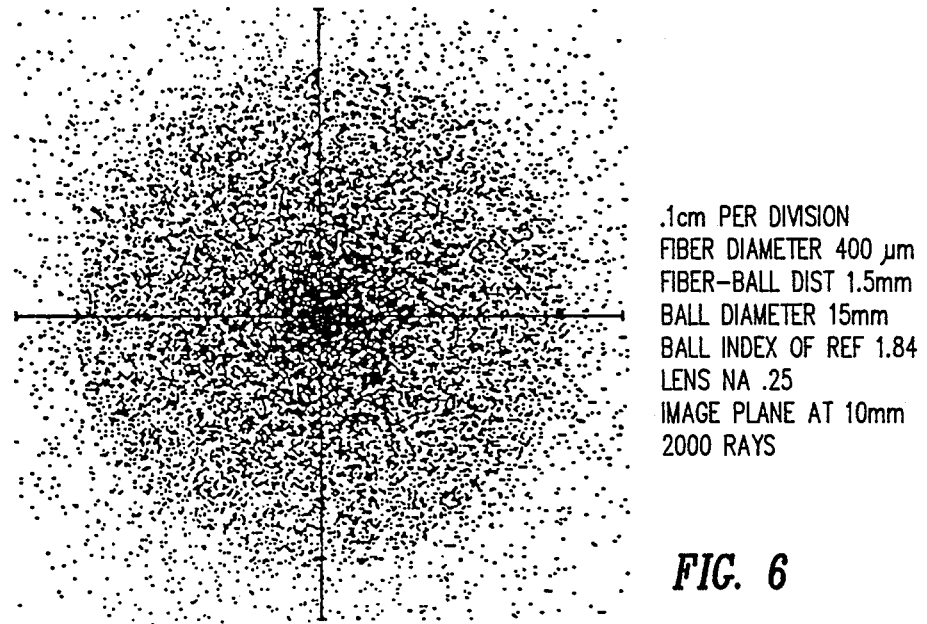
FIG. 6 illustrates a ray trace calculation of a typical optical radiation pattern when a ball lens is used.

FIG. 6 illustrates a ray trace calculation of a typical optical radiation pattern when a ball lens is used. The radiation pattern has a mean intensity of about 0.1 $W/cm^2$. By combining this data with the results shown in FIG. 5, and knowing that the noise floor for the PMT is about 0.05 microamps, the minimum detectable particle size is seen to be 0.15 microns, with a 10:1 signal-to-noise ratio at 0.2 microns.

It should be understood that the invention is not limited to the specific materials and parameters set forth above. Different types of optical fibers, lenses and lamps can be used within the scope of the invention. For example, a short wavelength laser such as He-Cd or Nd:YAG can be used instead of the mercury lamp.

What is claimed is:

1. A particle detector for use in a high temperature environment comprising:
    a light source for providing short wavelength radiation;
    an optical fiber means for receiving and conducting said radiation;
    means for focusing said radiation from said light source onto said optical fiber means;
    a process chamber to which said optical fiber means is directed;
    optical lens means for collimating or focusing the radiation passing through said optical fiber;
    an optical fiber pickup adjacent to said lens means for receiving light scattered by particles within said process chamber; and
    photosensing means to detect such scattered light and for producing pulse signals indicative of the number of particles that are present in said process chamber.

2. A particle detector as in claim 1, wherein said light source comprises a laser diode for producing short wavelength radiation.

3. A particle detector as in claim 1, wherein said light source comprises a short wavelength arc mercury vapor lamp.

4. A particle detector as in claim 1, wherein said photosensing means comprises a photodiode or a photomultiplier.

5. A particle detector as in claim 1, wherein said lens means comprises cylindrical and circular lenses that are symmetric for creating a light beam that is elliptical in shape.

6. A particle detector as in claim 1, including a filter positioned between said optical fiber pickup and said photosensing means for passing short wavelength radiation and for blocking long wavelength radiation from said photosensing means.

7. A particle detector as in claim 1, including a reflector adjacent to said light source for reflecting radiation that is emitted in a backward direction.

8. A particle detector as in claim 1, including a water filter disposed in said optical system for removing infrared light from said radiation.

9. A particle detector as in claim 1, wherein said optical fiber means consists essentially of quartz.

10. A particle detector as in claim 1, including feedthrough means coupled to said optical fiber means as it enters said process chamber.

11. A particle detector as in claim 1, wherein said optical fiber pickup comprises a bundle of fibers and a ferrule for holding said fiber bundle.

12. A method for detecting particles in high temperature process chambers comprising the steps of:
providing radiation having a short wavelength from a light source;
focusing said radiation from said light source onto one end of an optical fiber means;
conducting said radiation into a process chamber via said optical fiber means to provide light in said chamber from another end of said optical fiber means;
collimating or focusing said radiation received from said optical fiber means into a beam of light using an optical lens means;
receiving light scattered out of said beam by particles impacted by said beam of light at an end of an optical fiber pickup located in said chamber;
conducting said scattered light to an end of said optical fiber pickup located outside of said chamber; and
detecting said scattered light received from said optical fiber pickup using a photosensing means to provide an indication of the number of particles present in said process chamber.

13. A method for detecting particles in high temperature process chambers according to claim 12, further including the step of filtering infrared light from said radiation with a filtering means prior to focusing said radiation on said one end of said optical fiber means.

14. A method for detecting particles in high temperature process chambers according to claim 12, further including the step of filtering long wavelength light from said scattered light using a filtering means prior to detecting said scattered light by said photosensing means.

15. A method for detecting particles in high temperature process chambers according to claim 12, further including a reflector adjacent to said light source for reflecting radiation that is emitted in a backward direction.

16. A method for detecting particles in high temperature process chambers according to claim 12, further including feedthrough means coupled to said optical fiber means as it enters said process chamber.

17. A method for detecting particles in high temperature process chambers according to claim 12, wherein said photosensing means comprises a photodiode or a photomultiplier.

18. A method for detecting particles in high temperature process chambers according to claim 12, wherein said optical lens means comprises cylindrical and circular lenses that are symmetric for creating a light beam that is elliptical in shape.

19. A method for detecting particles in high temperature process chambers according to claim 13, wherein said filtering means is a water filter.

20. A method for detecting particles in high temperature process chambers according to claim 12, wherein said light source comprises a laser diode for producing short wavelength radiation.

21. A method for detecting particles in high temperature process chambers according to claim 12, wherein said light source comprises a short wavelength arc mercury vapor lamp.

22. A method for detecting particles in high temperature process chambers according to claim 12, wherein said optical fiber means consists essentially of quartz.

23. A method for detecting particles in high temperature process chambers according to claim 14, wherein said filtering means is positioned between said end of said optical fiber pickup located outside of said process chamber and said photosensing means for passing short wavelength radiation and for blocking long wavelength radiation from said photosensing means.

24. A method for detecting particles in high temperature process chambers according to claim 12, wherein said optical fiber pickup comprises a bundle of fibers and a ferrule for holding said fiber bundle.

25. A particle detection device for high temperature process chambers comprising:
a light source for providing short wavelength radiation;
an optical fiber means for receiving and conducting said radiation;
a focusing means for focusing said radiation from said light source onto one end of said optical fiber means;
a filtering means interposed in the light path between said light source and said optical fiber means for filtering infrared light from said radiation;
a process chamber into which said optical fiber means is directed;
an optical lens means within said process chamber for collimating or focusing the radiation passing out of said optical fiber means;
an optical fiber pickup having an end adjacent to said optical lens means for receiving light scattered by particles within said process chamber;
a photosensing means for detecting such scattered light and for producing pulse signals indicative of the number of particles that are present in said process chamber.

26. A particle detection device according to claim 25, further including another filtering means positioned in an operative relationship between said photosensing means and another end of said optical fiber pickup for filtering out long wavelength radiation from said light scattered by said particles.

27. A particle detection device according to claim 25, further including a reflector adjacent to said light source for reflecting radiation that is emitted in a backward direction.

28. A particle detection device according to claim 25, further including feedthrough means coupled to said optical fiber means as it enters said process chamber.

29. A particle detection device according to claim 25, wherein said photosensing means comprises a photodiode or a photomultiplier.

30. A particle detection device according to claim 25, wherein said optical lens means comprises cylindrical and circular lenses that are symmetric for creating a light beam that is elliptical in shape.

31. A particle detection device according to claim 25, wherein said light source comprises a laser diode for producing short wavelength radiation.

32. A particle detection device according to claim 25, wherein said light source comprises a short wavelength arc mercury vapor lamp.

33. A particle detection device according to claim 25, wherein said optical fiber means consists essentially of quartz.

34. A particle detection device according to claim 25, wherein said optical fiber pickup comprises a bundle of fibers and a ferrule for holding said fiber bundle.

35. A particle detection device according to claim 25, wherein said filtering means is a water filter.

36. A particle detection device according to any one of claims 1, 12 or 25, wherein said optical fiber means, said optical lens means and said optical fiber pickup all are uncoated.

* * * * *